United States Patent [19]

Natarajan et al.

[11] Patent Number: 4,749,792
[45] Date of Patent: Jun. 7, 1988

[54] DIAMINO KETONES AND ALCOHOLS AS ANALGESIC AGENTS

[75] Inventors: Sesha I. Natarajan, Neshanic Station; Eric M. Gordon, Pennington, both of N.J.

[73] Assignee: E. R. Squibb & Sons, Inc., Princeton, N.J.

[21] Appl. No.: 654,424

[22] Filed: Sep. 26, 1984

[51] Int. Cl.$^4$ .................... C07D 239/02; C07C 91/04; C07C 97/02

[52] U.S. Cl. .................... 546/312; 546/334; 548/337; 548/342; 548/483; 548/502; 549/68; 549/75; 549/76; 549/480; 549/492; 549/494; 560/169; 564/198; 564/240; 564/342; 564/344; 564/345; 564/355; 564/365; 564/366; 564/461; 564/500; 564/501; 564/502; 564/503; 564/511; 514/666; 514/667

[58] Field of Search ............... 564/502, 503, 511, 500, 564/501, 461, 198, 240, 342, 344, 345, 355, 365, 366; 424/325, 311; 560/169; 549/68, 75, 76, 480, 492, 494; 546/312, 334; 548/337, 342, 483, 507; 514/666, 667

[56] References Cited

U.S. PATENT DOCUMENTS 1,790,096  1/1931  Jensch ................. 564/503
2,253,081  8/1941  McNally et al. ........ 564/502

FOREIGN PATENT DOCUMENTS 1399262  8/1975  United Kingdom ........ 564/503

OTHER PUBLICATIONS

Zeller, E. A. et al., "(Substrates for Diamino Oxidase)" Helvetica Chimica Acta, vol. 39, pp. 1632–1644, (1956).
"Reactions of Some Halogeno Oxiranes with Methylamine and Dimethylamine" in J. of Org. Chem. of U.S.S.R., vol. 7, No. 2, pp. 236–238 (1971) (Malinovskii et al.).
"Substrate-Like Inhibitors of Diamine Oxidase" Macholàn in Archives of Biochemistry and Biophysics, vol. 134, No. 2, pp. 302–307.

Primary Examiner—Glennon H. Hollrah
Assistant Examiner—John A. Sopp
Attorney, Agent, or Firm—Lawrence S. Levinson; Donald J. Barrack

[57] ABSTRACT

Analgesic activity is exhibited by compounds having the formula

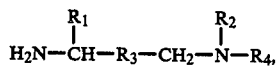

and pharmaceutically acceptable salts thereof wherein $R_1$, $R_2$ and $R_4$ are each independently hydrogen, alkyl, carboxyalkyl, halosubstituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl, and $R_3$ is hydroxymethylene or carbonyl.

9 Claims, No Drawings

DIAMINO KETONES AND ALCOHOLS AS ANALGESIC AGENTS

RELATED APPLICATION

U.S. patent application Ser. No. 515,729, filed July 21, 1983, discloses angiotensin converting enzyme inhibitors (hypotensive agents) having the formula

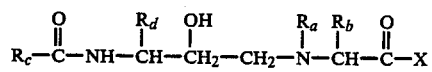

wherein X is an amino (or imino) acid residue, $R_a$ is hydrogen, alkyl, cycloalkyl, or specified substituted alkyl groups; $R_b$ is hydrogen, alkyl, or specified substituted alkyl groups; $R_c$ is specified substituted alkyl groups; and $R_d$ is hydrogen, alkyl or specified substituted alkyl groups which are prepared from the corresponding amino ketone having the formula

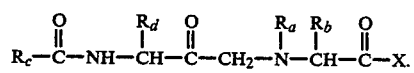

U.S. patent application Ser. Nos. 628,004, filed July 5, 1984 and 629,934, filed July 11, 1984, describe compounds having the formulas

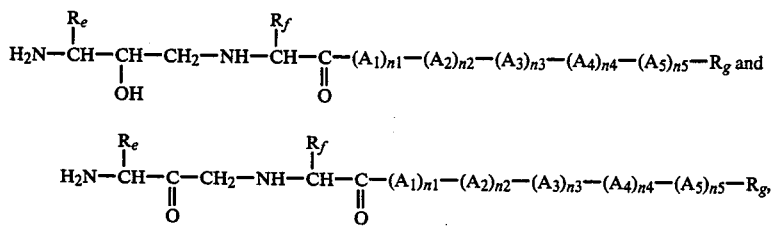

and pharmaceutically acceptable salts thereof, which possess inhibitory activity against an enkephalin-degrading aminopeptidase, and can be used as analgesic agents alone, or in conjunction with an enkephalinase inhibitor. In the above formulas $R_e$ and $R_f$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl; $R_g$ is hydroxy, alkoxy, (substituted alkyl)oxy, arylalkoxy, (heteroaryl)alkoxy, or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl; $A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

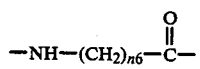

wherein $n_6$ is an integer of 2 to 15; $A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and $n_1$, $n_2$, $n_3$, $n_4$ and $n_5$ each is independently 0 or 1.

BRIEF DESCRIPTION OF THE INVENTION

Compounds having the formula

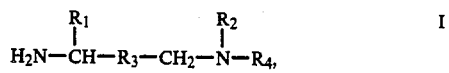

and pharmaceutically acceptable salts thereof, possess inhibitory activity against an enkephalin-degrading aminopeptidase, and can be used as analgesic agents alone, or in conjunction with an enkephalinase inhibitor.

In formula I, and throughout the specification, the symbols $R_1$, $R_2$ and $R_4$ are each independently hydrogen, alkyl, carboxyalkyl, halosubstituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl, and $R_3$ is hydroxymethylene or carbonyl.

The term "alkyl", as used throughout the specification, either individually or as part of a larger group, refers to straight and branched chain groups having 1 to 7 carbon atoms.

The term "halo substituted alkyl", as used throughout the specification either individually or as part of a larger group, refers to alkyl groups in which one, or more, hydrogens have been replaced by chloro, bromo or fluoro groups. Exemplary groups are trifluoromethyl, which is preferred, pentafluoroethyl, 2,2,2-trichloroethyl, chloromethyl and bromomethyl.

The term "cycloalkyl", as used throughout the specification either individually or as part of a larger group, refers to cycloalkyl groups having 3, 4, 5, 6 or 7 carbon atoms.

The term "substituted alkyl", as used throughout the specification, either individually or as part of a larger group, refers to alkyl groups substituted with one, or more (preferably one), hydroxy or $-NY_3Y_4$ groups, wherein $Y_3$ and $Y_4$ are the same or different and each is hydrogen or alkyl, $Y_3$ is hydrogen and $Y_4$ is aryl, or $Y_3$ and $Y_4$ together with the nitrogen atom to which they are attached form a heterocyclic group having the formula

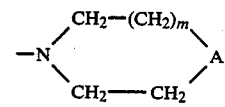

and A is CH—Q, oxygen, or N—Q, Q is hydrogen or alkyl and m is 0 or 1.

The term "heteroaryl", as used throughout the specification either individually or as part of a larger group, refers to 2- or 3-furanyl, 2- or 3-thienyl, 2-, 3- or 4-pyridinyl, 4-imidazolyl and 3-indolyl.

The term "aryl", as used throughout the specification either individually or as part of a larger group, refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

DETAILED DESCRIPTION OF THE INVENTION

The compounds of formula I, and the pharmaceutically acceptable salts thereof, can be administered to a mammalian specie as an analgesic agent due to their ability to inhibit an enkephalin-degrading aminopeptidase.

It is well known that the weak and short-lasting analgesic activity of endogenous enkephalins can be attributed to their rapid inactivation. Enkephalins are metabolized by several hydrolytic enzymes present in the brain: (1) aminopeptidases release the $Tyr^1$ residue, (2) a dipeptidyl aminopeptidase releases the $Tyr^1$-$Gly^2$ residue and (3) two enzymes cleave the penultimate $Gly^3$-$Phe^4$ bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism. The compounds of this invention inhibit the aminopeptidase activity and thus act as analgesic agents.

A compound of formula I, or a pharmaceutically acceptable salt thereof, can be administered to patients orally or parenterally in an effective amount within the daily dosage range of about 0.1 to about 25 milligrams of compound per kilogram of patient body weight. Administration can be once daily or in 2 to 4 divided daily doses.

The compounds of formula I can be prepared by coupling a halomethyl ketone having the formula

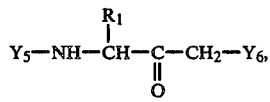

wherein $Y_5$ is an amino protecting group (e.g., a classical protecting group such as t-butoxycarbonyl, benzyloxycarbonyl, or o-nitrophenylsulfenyl) and $Y_6$ is chlorine or bromine, with a substituted amine having the formula

wherein $Y_7$ is an amino protecting group (such group being used when preparing a compound of formula I wherein $R_4$ is hydrogen), alkyl, carboxyalkyl, halosubstituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl, to yield a compound having the formula

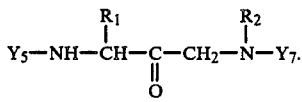

The reaction is preferably carried out in the presence of a base such as sodium bicarbonate, and sodium iodide is preferably added as a catalyst.

To obtain the compounds of formula I wherein $R_3$ is carbonyl, the corresponding compound of formula IV is deprotected using standard deprotection techniques. The particular deprotection reaction used will, of course, depend on the particular $Y_5$ and $Y_7$ groups present.

To obtain the compounds of formula I wherein $R_3$ is hydroxymethylene, a compound of formula IV is reduced using a chemical reducing agent such as sodium borohydride which is preferred, sodium cyanoborohydride, or a lithium trialkyl aluminum hydride to obtain a compound having the formula

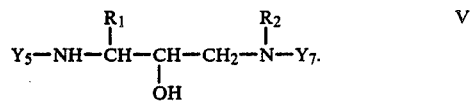

Deprotection of a compound of formula V using standard deprotection techniques yields the desired product of formula I wherein $R_3$ is hydroxymethylene.

Starting ketones of formula II can be prepared from amino acids having the formula

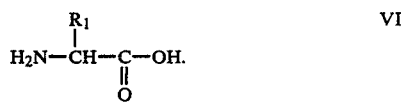

The amino group is first protected using, for example, a classical protecting group such as t-butyloxycarbonyl, benzyloxycarbonyl, or o-nitrophenylsulfenyl ($Y_5$), and yielding a compound having the formula

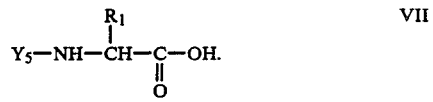

An activated form of an acid of formula VII (preferably a mixed anhydride) can be reacted with diazomethane to yield the corresponding diazo compound having the formula

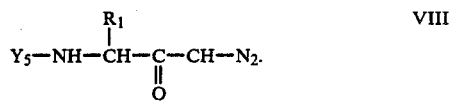

Reaction of a compound of formula VIII with hydrogen chloride or hydrogen bromide yields the corresponding compound having the formula

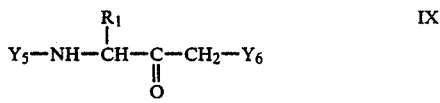

The compounds of formula I form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonates, (e.g., camphorsulfonate, benzenesulfonate, toluenesulfonate, etc.), citrate, ascorbate, maleate, fumarate, pamoate, acetate, tartrate, salicylate and the like. It is frequently convenient to isolate the compound by forming the acid salt and precipitating in a medium in which it is insoluble.

Products of formula I may have one, or more, asymmetric carbon atoms. If $R_1$ is other than hydrogen, the carbon atom to which it is attached will be asymmetric. The compounds, therefore, may exist in stereoisomeric forms, and as racemic mixtures thereof. All of these are within the scope of this invention. The above-described syntheses can utilize the racemate or one of the diastereomers as the starting material. When the racemic starting material is used in the synthetic procedure, the stereoisomers obtained in the product can be separated by conventional chromatographic or fractional crystallization techniques.

Preferred compounds of this invention are those wherein $R_4$ is hydrogen. Also preferred are those compounds wherein $R_1$ and $R_2$ are independently phenylmethyl, 2-methylpropyl, aminopropyl, aminobutyl or guanidinylpropyl. Exemplary of these preferred compounds are the following:

$$H_2N-\underset{R_1}{\underset{|}{CH}}-R_3-\underset{R_2}{\underset{|}{CH_2}}-NH$$

| $R_1$ | $R_2$ | $R_3$ |
|---|---|---|
| C$_6$H$_5$-CH$_2$- | (CH$_3$)$_2$CH-CH$_2$- | -CH(OH)- |
| C$_6$H$_5$-CH$_2$- | (CH$_3$)$_2$CH-CH$_2$- | -C(=O)- |
| C$_6$H$_5$-CH$_2$- | C$_6$H$_5$-CH$_2$- | -CH(OH)- |
| C$_6$H$_5$-CH$_2$- | C$_6$H$_5$-CH$_2$- | -C(=O)- |
| NH$_2$-(CH$_2$)$_4$- | NH$_2$-(CH$_2$)$_4$- | -CH(OH)- |
| NH$_2$-(CH$_2$)$_4$- | NH$_2$-(CH$_2$)$_4$- | -C(=O)- |
| NH$_2$-(CH$_2$)$_4$- | (CH$_3$)$_2$CH-CH$_2$- | -CH(OH)- |
| NH$_2$-(CH$_2$)$_4$- | (CH$_3$)$_2$CH-CH$_2$- | -C(=O)- |
| (CH$_3$)$_2$CH-CH$_2$- | C$_6$H$_5$-CH$_2$- | -CH(OH)- |
| (CH$_3$)$_2$CH-CH$_2$- | C$_6$H$_5$-CH$_2$- | -C(=O)- |
| NH$_2$-C(=NH)-NH-(CH$_2$)$_3$- | (CH$_3$)$_2$CH-CH$_2$- | -CH(OH)- |
| NH$_2$-C(=NH)-NH-(CH$_2$)$_3$- | (CH$_3$)$_2$CH-CH$_2$- | -C(=O)- |

-continued $$H_2N-\underset{R_1}{\underset{|}{CH}}-R_3-\underset{R_2}{\underset{|}{CH_2}}-NH$$

| $R_1$ | $R_2$ | $R_3$ |
|---|---|---|
| NH$_2$-(CH$_2$)$_3$- | (CH$_3$)$_2$CH-CH$_2$- | -CH(OH)- |
| NH$_2$-(CH$_2$)$_3$- | (CH$_3$)$_2$CH-CH$_2$- | -C(=O)- |
| (CH$_3$)$_2$CH-CH$_2$- | NH$_2$-(CH$_2$)$_3$- | -CH(OH)- |
| (CH$_3$)$_2$CH-CH$_2$- | NH$_2$-(CH$_2$)$_3$- | -C(=O)- |

The following examples are specific embodiments of this invention.

EXAMPLE 1

(S)-3-Amino-5-methyl-1-[(2-methylpropyl)amino]-2-hexanone, dihydrochloride (A) N-Benzylidene-2-methyl-1-propanamine To a stirred solution of isobutylamine (49.7 ml, 500 mmol) in dry benzene (50 ml) was added benzaldehyde (50.8 ml, 500 mmol) over a period of 20 minutes. After three hours, the water layer was separated and the stirring of the benzene solution continued overnight. Again the separated water layer was discarded. The benzene layer after further dilution with dry benzene (150 ml) was dried over a minimum amount of magnesium sulfate. After concentrating the dried benzene solution, the residue was distilled in vacuo, yielding 72.1 g of compound, boiling point 46°-48° C. at 0.1 mm of Hg.

(B) (2-Methylpropyl)(phenylmethyl)amine

To a stirred solution of lithium aluminum hydride (23 g, 606 mmol) in ether (115 ml) was added an ethereal solution (115 ml) of N-benzylidene-2-methyl-1-propanamine (72.1 g, 447 mmol) over a period of 45 minutes. It was then refluxed for one hour. The reaction mixture was cooled in an ice bath and while stirring vigorously, aqueous sodium hydroxide (20%, 120 ml) was added dropwise. The ether solution was separated, dried over magnesium sulfate and concentrated to dryness yielding 66.1 g of the title compound.

(C) [(t-Butyloxy)carbonyl]-L-leucine diazomethyl ketone

To a stirred solution of [[(t-butyloxy)carbonyl]amino]-L-leucine (34.67 g, 150 mmol) in dry tetrahydrofuran (135 ml) at $-15°$ C., N-methylmorpholine (16.5 ml, 150 mmol) was added followed by the dropwise addition of isobutyl chloroformate (19.5 ml, 150 mmol). After stirring at $-15°$ C. for 12 minutes, the solution was filtered and diluted with ether (400 ml) kept at $-20°$ C. This was added dropwise over 15 minutes to an ethereal solution of diazomethane (600 ml, generated from 60 g of N-methyl-N$^1$-nitro-N-nitrosoguanidine). After the addition was over, the reaction was allowed to run at room temperature for two hours. Excess diazomethane was blown off by a stream of nitrogen. The ethereal solution was washed with saturated aqueous sodium bicarbonate and saturated sodium chloride solutions. The etheral solution was concentrated in vacuo and the residue was dissolved in hexane. On cooling, the title compound was obtained as crystals (27.7 g, melting point 89°–90° C.).

(D) [(t-Butyloxy)carbonyl]-L-leucine chloromethyl ketone

To a stirred (ice bath) solution of (2-methylpropyl)(-phenylmethyl)amine (24 g, 94 mmol) in ether (470 ml) was added hydrogen chloride in acetic acid (2.2N, 94 mmol) dropwise. After stirring for ten minutes, it was evaporated in vacuo. The residue was dissolved in ethyl acetate:hexane (1:3) and passed through a small column of silica gel (400 g) using the same solvent system for elution. The title compound was obtained as a homogeneous material (23.2 g). On crystallization from a mixture of ether and hexane, fine crystals of the title compound were obtained, melting point 66°–68° C.

(E)
(S)-[3-Methyl-1-[[(2-methylpropyl)(phenylmethyl)amino]acetyl]butyl]carbamic acid, 1,1-dimethylethyl ester, 4-methylbenzenesulfonic acid salt A solution of (2-methylpropyl)(phenylmethyl)amine (8.16 g, 50 mmol), [(t-butyloxy)carbonyl]-L-leucine chloromethyl ketone (13.19 g, 50 mmol), sodium bicarbonate (6.3 g, 75 mmol), sodium iodide (3.74 g, 25 mmol) and dimethylformamide (100 ml) was stirred at room temperature for four hours. It was then evaporated, taken into ethyl acetate and washed with water. The ethyl acetate solution was evaporated and the residue dissolved in ether. The ethereal solution was filtered to remove a very small amount of insoluble material. The ethereal solution was evaporated and the residue was chromatographed over a small column of silica gel (350 g) using the solvent system ethyl acetate:hexane (1:4). The homogeneous fractions were pooled and evaporated (17.62 g). The residue was dissolved in ether and an ethyl acetate solution of p-toluenesulfonic acid (8.6 g, 45.2 mmol) was added. The crystallized material was filtered yielding 18.72 g of the title compound, melting point 143° C., $[\alpha]_D^{22} = -38.9°$ (c, 2.2, methanol).

(F)
(S)-[4-Methyl-1-[[(2-methylpropyl)amino]acetyl]butyl]carbamic acid, 1,1-dimethylethyl ester, hydrochloride (S)-[3-Methyl-1-[[(2-methylpropyl)(phenylmethyl)amino]acetyl]butyl]carbamic acid, 1,1dimethylethyl ester, 4-methylbenzenesulfonic acid salt (2.25 g, 4 mmol) was taken into ethyl acetate and shaken with saturated sodium bicarbonate to liberate the free amine. The ethyl acetate solution was evaporated and the residue was dissolved in methanol (30 ml). After adding hydrochloric acid (1N, 4 ml) and palladium hydroxide on carbon catalyst (0.3 g), the solution was stirred under an atmosphere of hydrogen for 90 minutes. It was then filtered through Hyflo and evaporated to dryness (1.32 g). A portion of this crude product (0.64 g) was crystallized from ether yielding 0.445 g of the title compound, melting point 113°–115° C.

(G)
(S)-3-Amino-5-methyl-1-[(2-methylpropyl)amino]-2-hexanone, dihydrochloride (S)-[4-Methyl-1-[[(2-methylpropyl)amino]acetyl]butyl]carbamic acid, 1,1-dimethylethyl ester, hydrochloride (0.66 g, 1.95 mmol) was dissolved in a solution of hydrogen chloride in acetic acid (1.5N, 7 ml) and allowed to stand at room temperature for 20 minutes. It was evaporated in vacuo and then re-evaporated from benzene. The residue was crystallized from isopropanol yielding 240 mg of the title compound, melting point 148°–150° C.

Analysis Calc'd. for $C_{11}H_{24}N_2O.2HCl.0.28MH_2O$: C, 47.48; H, 9.62; N, 10.07; Cl: 25.48 Found: C, 47.48; H, 9.54; N, 9.97; Cl, 25.48

EXAMPLE 2

(2±,3S)-3-Amino-5-methyl-1-[(2-methylpropyl)amino]-2-hexanol, dihydrochloride (A)
(S)-[1-[(RS)-1-Hydroxy-2-[(2-methylpropyl)(phenylmethyl)amino]ethyl]-3-methylbutyl]carbamic acid, 1,1-dimethylethyl ester, hydrochloride (S)-[3-Methyl-1-[[(2-methylpropyl)(phenylmethyl)amino]acetyl]butyl]carbamic acid, 1,1dimethylethyl ester, 4-methylbenzenesulfonic acid salt (5.62 g, 10 mmol; see example 1E) was taken into ethyl acetate and shaken with saturated sodium bicarbonate solution. The ethyl acetate layer was dried over magnesium sulfate and evaporated in vacuo (3.9 g). This free base was dissolved in ethanol (35 ml). While stirring the ethanolic solution at room temperature, sodium borohydride (400 mg, 10.4 mmol) was added. After one hour, the solution was evaporated. The residue was suspended in ethyl acetate and water and acidified to pH 2.0 using dilute hydrochloric acid, and then saturated sodium bicarbonate solution was added until the solution was slightly basic. The ethyl acetate layer was dried over magnesium sulfate and evaporated (3.91 g). To an ethereal solution of an aliquot of the above alcohol (0.559 g, 1.42 mmol), hydrogen chloride in dioxane solution (5N, 0.28 ml) was added. The solution was concentrated and dried in high vacuum. The title compound was obtained as a solid, melting point 50°–65° C.

(B)
[(S)-1-[1-Hydroxy-2-[(2-methylpropyl)amino]ethyl]-3-methylbutyl]carbamic acid, 1,1-dimethylethyl ester, hydrochloride (S)-[1-[(RS)-1-Hydroxy-2-[(2-methylpropyl)(phenylmethyl)amino]ethyl]-3-methylbutylcarbamic acid, 1,1-dimethylethyl ester, hydrochloride (1.67 g, 4.25 mmol) was dissolved in methanol (50 ml) and hydrochloric acid (1N, 4.25 ml) was added. The solution was stirred under an atmosphere of hydrogen in the presence of palladium hydroxide on carbon catalyst (0.36 g) for two hours. It was filtered through Hyflo and concentrated to dryness in vacuo (1.31 g).

(C)
(2±,3S)-3-Amino-5-methyl-1-[(2-methylpropyl)amino]-2-hexanol, dihydrochloride

[(S)-1-[1-Hydroxy-2-[(2-methylpropyl)amino]ethyl]-3-methylbutyl]carbamic acid, 1,1-dimethylethyl ester, hydrochloride (0.678 g, 2 mmol) was suspended in a solution of hydrogen chloride in dioxane (1.5N, 6.6 ml);

it did not dissolve readily. Additional hydrogen chloride in dioxane (5N, 1 ml) and methanol (2.3 ml) were added whereupon it became a homogeneous solution. After two hours at room temperature, the solution was concentrated to dryness and dried at high vacuum overnight, yielding 0.55 g of product, melting point 195°-200° C.

Analysis Calc'd. for $C_{11}H_{26}N_2O \cdot 2HCl$: C, 48.0; H, 10.25; N, 10.18; Cl, 25.76 Found: C, 47.84; H, 9.96; N, 10.09; Cl, 25.52

What is claimed is:

1. A compound having the formula

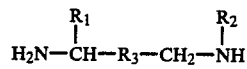

or a pharmaceutically acceptable salt thereof, wherein $R_1$ or $R_2$ are each independently alkyl, carboxyalkyl, halo-substituted alkyl, hydroxyalkyl, aminoalkyl, mercaptoalkyl, alkylthioalkyl, (cycloalkyl)alkyl, (heteroaryl)alkyl, and $R_3$ is hydroxymethylene or carbonyl.

2. A compound having the formula

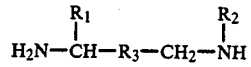

or a pharmaceutically acceptable salt thereof, wherein $R_1$ and $R_2$ are each independently alkyl, carboxyalkyl, halo-substituted alkyl, hydroxyalkyl, aminoalkyl, mercaptoalkyl, alkylthioalkyl, or (cycloalkyl)alkyl and $R_3$ is hydroxymethylene or carbonyl.

3. A compound in accordance with claim 2 wherein $R_3$ is hydroxymethylene.

4. A compound in accordance with claim 2 wherein $R_3$ is carbonyl.

5. A compound in accordance with claim 1 wherein $R_1$ and $R_2$ are each independently phenylmethyl, 2-methylpropyl, aminopropyl, aminobutyl, or guanidinylpropyl.

6. A compound in accordance with claim 2 wherein $R_1$ and $R_2$ are each alkyl.

7. A compound in accordance with claim 6 wherein $R_1$ and $R_2$ are each 2-methylpropyl.

8. The compound in accordance with claim 2 (S)-3-amino-5-methyl-1-[(2-methylpropyl)amino]-2-hexanone, or a pharmaceutically acceptable salt thereof.

9. The compound in accordance with claim 2, (2±,3S)-3-amino-5-methyl-1-[(2-methylpropyl)amino]-2-hexanol, or a pharmaceutically acceptable salt thereof.

* * * * *

UNITED STATES PATENT AND TRADEMARK OFFICE
CERTIFICATE OF CORRECTION

PATENT NO. : 4,749,792

DATED : June 7, 1988

INVENTOR(S) : Sesha I. Natarajan; Eric M. Gordon

It is certified that error appears in the above-identified patent and that said Letters Patent is hereby corrected as shown below:

In column 9, line 24, "or" should be --and--.

In column 9, line 27, after "ryl)alkyl," should be added --arylalkyl, carbamoylalkyl, guanidinylalkyl or heteroaryl,--.

Signed and Sealed this

First Day of November, 1988

Attest:

DONALD J. QUIGG

*Attesting Officer*          *Commissioner of Patents and Trademarks*